United States Patent [19]

Lukehart

[11] 4,089,881

[45] May 16, 1978

[54] COMPLEXES OF METALLATED COORDINATION LIGANDS

[75] Inventor: Charles M. Lukehart, Nashville, Tenn.

[73] Assignee: Vanderbilt University, Nashville, Tenn.

[21] Appl. No.: 741,390

[22] Filed: Nov. 12, 1976

[51] Int. Cl.$^2$ ............................................. C07F 13/00
[52] U.S. Cl. ........................... 260/429 R; 252/431 C; 252/431 N; 252/431 P; 252/431 R; 260/429 J; 260/439 CY; 260/439 R
[58] Field of Search ........ 260/439 R, 439 CY, 429 R, 260/429 J, 429.9; 252/431 R, 431 C, 431 N, 431 P

[56] References Cited

U.S. PATENT DOCUMENTS

| | | | |
|---|---|---|---|
| 3,159,660 | 12/1964 | Closson et al. | 260/439 CY |
| 3,268,565 | 8/1966 | Fischer et al. | 260/439 CY |
| 3,398,167 | 8/1968 | Mahler | 260/429 R |
| 3,449,388 | 6/1969 | Lewis et al. | 260/429 R |
| 3,539,606 | 11/1970 | Murdoch et al. | 260/429 R |
| 3,739,003 | 6/1973 | Codet et al. | 260/439 R |
| 3,857,867 | 12/1974 | Maspero et al. | 260/429 R |
| 3,980,730 | 9/1976 | Dawans et al. | 260/429 R |

OTHER PUBLICATIONS

Casey et al., J.C.S. Chem. Comm. p.733, (1974).
Treichel et al., Inorganic Chemistry 10, 1183–1187 (1971).
Lukehart et al., J.A.C.S. 97 6903–6904 (1975).
Dobson et al., J.A.C.S. 95 5925–5930 (1973).
Johnson et al., Inorg. Chem. 10 2091–2095 (1971).
Casey et al., J.A.C.S. 98 436–440 (1976).
Fischer et al., Chem. Ber. 100 2445–2446 (1967).
Block et al., J.A.C.S. 98 441–443 (1976).

*Primary Examiner*—Helen M. S. Sneed
*Attorney, Agent, or Firm*—Harrington A. Lackey

[57] ABSTRACT

The present invention relates to organometallic complexes which contain at least two metal atoms, or a metal atom and a proton, and at least one ligand representing a metallated unsaturated chelating six-membered ring system, where the metallation involves the formal replacement of a methine group by an organometallic complex.

The compounds of the invention have utility as both homogeneous and heterogeneous catalysts of hydrogenation, polymerization, isomerization, hydroformylation and metathetical exchange reactions.

38 Claims, 2 Drawing Figures

COMPLEXES OF METALLATED COORDINATION LIGANDS

BACKGROUND OF THE INVENTION

This invention relates to organometallic compounds, and more particularly to complexes of metallated coordination ligands, and the process of making such complexes.

Some metal analogs of acetylacetone are known for use as catalysts for polymerization. Some acyl pentacarbonyl metallates, such as acetylpentacarbonylmanganese, are known catalysts for hydroformylation.

SUMMARY OF THE INVENTION

According to this invention, organometallic compounds having the general structural formula:

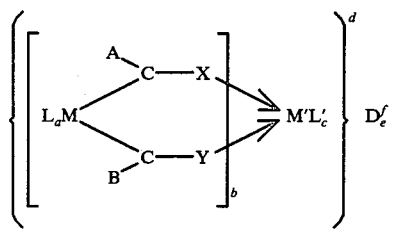

have been developed for use as homogeneous and heterogeneous catalysts of hydrogenation, polymerization, isomerization, hydroformylation and metathetical exchange reactions.

The general empirical formula is $((L_aM[C(X)A][C(Y)B])_bM'L'_c hd\ c)^d\ D_e^f$, in which M is a transition metal and M' may be any metal atom, except lithium or magnesium, or a proton; L and L' are coordinating ligands selected from the group consisting of at least one of CO, $PF_3$, $PCl_3$, $PBr_3$, $PR_3$, $P(OR)_3$, $AsR_3$, NCO, CN, $NR_3$, halogen, R, OR, CNR, NO, C(O)R, in unsaturated form having from 1 to 20 carbon atoms; R is a hydrocarbyl radical having from 1 to 20 carbon atoms, such as saturated alkyl and cycloalkyl radicals having from 1 to 20 carbon atoms and unsaturated alkyl and cycloalkyl radicals having from 2 to 20 carbon atoms, and phenyl and substituted phenyl radicals having from 6 to 20 carbon atoms; X and Y are atoms or radicals selected from the group consisting of at least one of O, S, Se, NR, PR, where R is as above; A and B are substituents consisting of at least one of R, OR, $NR_2$, SR, SeR, $PR_2$, CN, where R is as above; D is a counter-ion of charge f selected, as an example, from the group consisting of halogen, $BF_4$, $PF_6$, $NO_3$, $SO_4$, $PO_4$, $ClO_4$, Li, Na, K, Rb, Cs, Mg, Ca, Sr, Ba; $a$ is an integer from 1 to 10 inclusive; $b$ is an integer from 1 to 6 inclusive; $c$ is an integer from zero to 10 inclusive; $d$ is an integer from $-4$ to $+4$ inclusive, and including zero; $e$ is an integer from zero to 4 inclusive; $f$ is an integer other than zero from $-4$ to $+4$ inclusive, where $d + ef = 0$.

For example, when $a$ is 4, $b$ is 3, $c$ and $d$ and $e$ are all zero, L is carbon monoxide, X and Y are both oxygen atoms, and A and B are both methyl radicals, the product is $((OC)_4M[C(O)CH_3][C(O)CH_3])_3M'$ having a molecular weight of 786.20, when M is manganese and M' is aluminum, and a molecular weight of 960.23 when M is rhenium and M' is gallium.

The preferred method of preparation of the compounds of the present invention is to treat by admixture in an inert atmosphere an organometallic compound containing M, $L_a$, C(X)A and C(Y) with a nucleophilic reagent acting as the source of the anion of B, such as a lithium, Grignard, Reformatsky or other alkylating or nucleophilic reagents, using the approximate stoichiometric amounts, followed by the mixing in of a source of M' which is soluble in the solvent used, such as the anhydrous metal halide or acid, using the approximate stoichiometric amount. The temperature is not a critical variable and may be maintained in the range of from $-78°$ to $25°$ C. The pressure is likewise not critical, although atmospheric pressure may be desirable.

The present process employs the presence of a solvent to provide a mixing of the reagents. Various polar organic solvents may be employed such as ethers, for example, diethyl ether or tetrahydrofuran, acetone, methylene chloride and chloroform. Water may be used in special cases. The proportion of solvent is not critical.

The reaction may be followed by various spectroscopic techniques, such as nuclear magnetic resonance and infrared spectroscopy, by removing a sample of the reaction solution at various time intervals throughout the reaction. After the reaction appears to be complete, the solvent can be removed. The product can be extracted into a solvent and isolated pure by fractional crystallization. Other methods which may be used to obtain the products of the present invention include solvent extraction and column chromatography.

DESCRIPTION OF THE PREFERRED EMBODIMENTS

Example 1

Tris(cis-diacetyltetracarbonylmanganate) aluminum is prepared by mixing together 1.0 g (4.2 millimoles) of acetylpentacarbonylmanganese in 5 milliliters of diethyl ether at 0° C. with 4.5 millimoles of methyllithium solution in diethyl ether over a 10 minute period followed by the addition of 1.4 millimoles of anhydrous aluminum (III) chloride as a solution is diethyl ether. After stirring the reaction mixture for one hour the solvent is removed at reduced pressure.

The reaction can be followed by infrared spectroscopy by removing samples of the reaction solution at various times during the reaction. The reaction of methyllithium with acetylpentacarbonylmanganese is indicated by the decrease in intensity of the band arising from the stretching mode of the acyl group at 1560 $cm^{-1}$ and the appearance of a band at 1585 $cm^{-1}$ belonging to the anionic intermediate.

The product is isolated by dissolving in methylene chloride, followed by filtration and the removal of the solvent from the filtrate at reduced pressure. The product is air stable for at least 24 hours and decomposes rapidly when heated to 265° C. The product ((OC)₄Mn[C(O)CH₃] [C(O)CH₃])₃Al has the empirical formula Mn₃AlO₁₈C₂₄H₁₈. The product is soluble in saturated hydrocarbons such as cyclohexane, hexane, pentane, octane, dodecane and unsaturated hydrocarbons such as benzene, toluene, xylene, mesitylene and chlorocarbon solvents such as methylene chloride, chloroform, carbon tetrachloride, and in methanol, acetone, diethyl ether, carbon disulfide, tetrahydrofuran and ethyl acetate.

Figure 1:
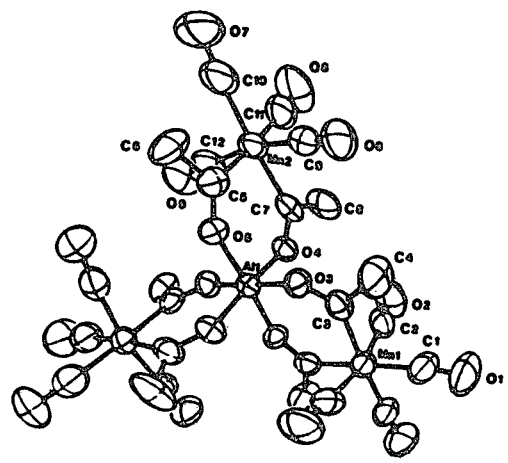
FIG. 1 is a perspective view of the molecular structure of one of the independent molecules of $((OC)_4Mn [C(O)CH_3] [C(O)CH_3])_3Al$, showing the atomic numbering scheme, excluding the hydrogen atoms.

The three-dimensional molecular structure, excluding the hydrogen atoms, of this product is shown in FIG. 1.

The structure of the product tris(cis-diacetyltetracarbonylmanganate) aluminum is proven by the following:

(A) The proper elemental analysis;

(B) Nuclear magnetic resonance data. A single H¹-NMR peak at 7.28 τ in deuterated chloroform solution in accordance with the six equivalent methyl groups;

(C) Infrared spectroscopic data. Four peaks due to the carbon monoxide ligands at 2065 cm⁻¹, 1985 cm⁻¹, 1978 cm⁻¹, and 1960 cm⁻¹, in accordance with a cis- and disubstituted octahedral complex containing four other carbon monoxide ligands, and a band at 1525 cm⁻¹ from the carbon-oxygen band stretch of the coordinated acetyl groups all recorded in cyclohexane solution;

(D) The complete single-crystal X-ray structural determination of the crystal and molecular structure. This evidence demonstrates the only slightly distorted octahedral local symmetry around all four metal atoms, the essentially planar and symmetrical nature of the ligand ring systems and the fact that all six axial carbon monoxide ligands on the manganese atoms are bent slightly toward the aluminum atom as if to bond weakly to the pi-electron system of the chelate ligand which is coordinated to the aluminum ion.

Example 2

Tris(cis-acetyldimethylcarboxamidotetracarbonyl manganate) aluminum is prepared by mixing together 1.5 g (6.5 millimoles) of acetylpentacarbonylmanganese in 50 milliliters of tetrahydrofuran at −78° C. with 8.0 millimoles of lithium dimethylamide solution in tetrahydrofuran over a 30 minute period followed by the addition of 2.1 millimoles of anhydrous aluminum (III) chloride as a solution in tetrahydrofuran. After stirring the reaction at 0° C. for two hours, the solvent is removed at reduced pressure and the product is isolated by extracting into methylene chloride solvent and filtering, followed by removal of the solvent from the filtrate at reduced pressure, followed by extracting this residue into hexane and filtering, followed by removal of the solvent from the filtrate at reduced pressure. The major compound in this residue is the product and it may be purified by fractional crystallization from hexane solution.

The product is air stable for at least short periods of time and decomposes slowly when heated in air at 125° C. with more rapid decomposition at 250° C. The product ((OC)₄Mn[C(O)CH₃] [C(O)N(CH₃)₂])₃Al has the empirical formula Mn₃AlO₁₈N₃C₂₇H₂₇. The product is soluble in the solvents listed in Example 1.

The structure of the product tris(cis-acetyldimethylcarboxamidotetracarbonylmanganate) aluminum is proven by the following:

(A) The proper elemental analysis;

(B) Nuclear magnetic resonance data. The H¹-NMR data show the methyl resonances of the acetyl and the dimethylcarboxamido groups with an intensity ratio of 1:2, respectively.

(C) Infrared spectroscopic data. The spectrum of a cyclohexane solution of the product shows the four bands due to the carbon monoxide ligands and the acyl C—O band at 1525 cm⁻¹.

Example 3

Tris(cis-acetylcarboethoxytetracarbonylmanganate) aluminum is prepared by mixing together 1.0 g (3.73 millimoles) of carboethoxypentacarbonylmanganese in 15 milliliters of diethyl ether at −78° C. with 4.0 millimoles of methyllithium solution in diethyl ether over a 30 minute period followed by the addition of 1.3 millimoles of anhydrous aluminum chloride dissolved in 3 milliliters of diethyl ether. The reaction is stirred at 0° C. for two additional hours and the product is isolated and purified by the procedure of EXAMPLE 2.

The product ((OC)₄Mn[C(O)OC₂H₅] [C(O)CH₃])₃Al has the empirical formula Mn₃AlO₂₁C₂₇H₂₄ and is soluble in the solvents listed in EXAMPLE 1 and is identified by infrared spectroscopy.

Example 4

Tris(cis-acetyl-iso-butyryltetracarbonylmanganate aluminum is prepared by treating 1.0 g (3.76 millimoles) of iso-butyrylpentacarbonyl manganese with 3.80 millimoles of methyllithium and 1.26 millimoles of anhydrous aluminum chloride following the procedure of EXAMPLE 1, the product ((OC)₄Mn[C(O)CH(CH₃)₂][C(O)CH₃]₃Al is obtained as the major product and is identified by proton magnetic resonance, elemental analysis and infrared spectroscopy.

Example 5

When the procedure of EXAMPLE 1 is used with 4 millimoles of acetylpentacarbonylrhenium and 4.1 millimoles of methyllithium and 1.35 millimoles of anhydrous aluminum chloride in 20 milliliters of diethyl ether as the solvent, with reaction being conducted at 0° C., the major product is tris(cis-diacetyltetracarbonylrhenate) aluminum ((OC)₄Re[C(O)CH₃][C(O)CH₃])₃Al which has the empirical formula Re₃AlO₁₈C₂₄H₁₈. The product is identified by proton magnetic resonance, elemental analysis and infrared spectroscopy.

Example 6

When the procedure of EXAMPLE 1 is used with 4 millimoles of acetylpentacarbonylrhenium and 4.1 millimoles of methyllithium and 1.34 millimoles of anhydrous gallium (III) chloride in 15 milliliters of diethyl ether as the solvent, with reaction being conducted at 0°

C., the major product is tris-(cis-diacetyltetracarbonylrhenate) gallium ((OC)$_4$Re[C(O)CH$_3$][C(O)CH$_3$])$_3$Ga which has the empirical formula Re$_3$GaO$_{18}$C$_{24}$H$_{18}$. The product is identified by proton magnetic resonance, elemental analysis and infrared spectroscopy.

Example 7

When the procedure of EXAMPLE 1 is used with 4 millimoles of iso-butyrylpentacarbonylrhenium and 4.1 millimoles of methyllithium and 1.34 millimoles of anhydrous gallium (III) chloride in 15 milliliters of diethyl ether as the solvent, with reaction being conducted at 0° C., the major product is tris-(cis-acetyl-isobutyryltetracarbonylrhenate) gallium ((OC)$_4$Re[C(O)CH(CH$_3$)$_2$][C(O)CH$_3$])$_3$Ga which has the empirical formula Re$_3$GaO$_{18}$C$_{30}$H$_{30}$. The product is identified by proton magnetic resonance, elemental analysis and infrared spectroscopy.

Example 8

When the procedure of EXAMPLE 1 is used with 4.0 millimoles of acetylpentacarbonylrhenium and 4.1 millimoles of methyllithium and 2.0 millimoles of anhydrous cobalt (II) tetrafluoroborate in 20 ml of tetrahydrofuran as the solvent with reaction being conducted at 0° C., the major product is bis-(cis-diacetyltetracarbonylrhenate) cobalt.

((OC)$_4$Re[C(O)CH$_3$][C(O)CH$_3$])$_2$Co

Example 9

This product is prepared by the procedure of EXAMPLE 1 using propionylpentacarbonylmanganese in place of acetylpentacarbonylmanganese.

((OC)$_4$Mn[C(O)CH$_2$CH$_3$][C(O)CH$_3$])$_3$Al

Example 10

This product is prepared by the procedure of EXAMPLE 1 using benzyrylpentacarbonylmanganese in place of acetylpentacarbonylmanganese.

((OC)$_4$Mn[C(O)CH$_2$(C$_6$H$_5$)][C(O)CH$_3$])$_3$Al

Example 11

This product is prepared by the procedure of EXAMPLE 1 using n — butyllithium in place of methyllithium.

((OC)$_4$Mn[C(O)CH$_3$][C(O)CH$_2$(CH$_2$)$_2$CH$_3$])$_3$Al

Example 12

This product is prepared by the procedure of EXAMPLE 1 using isobutyrylpentacarbonylmanganese in place of acetylpentacarbonylmanganese and n — butyllithium in place of methyllithium.

((OC)$_4$Mn[C(O)CH(CH$_3$)$_2$][C(O)CH$_2$(CH$_2$)$_2$CH$_3$])$_3$Al

Example 13

This product is prepared by the procedure of EXAMPLE 5 using anhydrous scandium chloride in place of the anhydrous aluminum chloride.

((OC)$_4$Re[C(O)CH$_3$][C(O)CH$_3$])$_3$Sc

Example 14

This product is prepared by the procedure of EXAMPLE 1 using cis-(methylisocyanide) acetyltetracarbonylmanganese in place of acetylpentacarbonylmanganese.

((CH$_3$NC) (OC)$_3$Mn[C(O)CH$_3$][C(O)CH$_3$])$_3$Al

Example 15

This product is prepared by the procedure of EXAMPLE 1 using cis-(cyclohexylisocyanide) acetyltetracarbonylmanganese in place of acetylpentacarbonylmanganese.

((C$_6$H$_{11}$NC) (OC)$_3$Mn[C(O)CH$_3$][C(O)CH$_3$])$_3$Al

Example 16

This product is prepared by the procedure of EXAMPLE 5 using 2 millimoles of anhydrous zinc chloride in place of the 1.35 millimoles of anhydrous aluminum chloride.

((OC)$_4$Re[C(O)CH$_3$][C(O)CH$_3$])$_2$Zn

Example 17

This product is prepared by the procedure of EXAMPLE 1 using $\pi$-cyclopentadienyldicarbonylacetyliron in place of acetylpentacarbonylmanganese and using a reaction temperature of −50° C. for the addition and stirring of all of the reagents, followed by stirring the reaction solution at −10° C. for an additional hour.

(($\pi$—C$_5$H$_5$) (OC)Fe[C(O)CH$_3$][C(O)CH$_3$])$_3$Al

Example 18

This product is prepared by the procedure of EXAMPLE 17 using $\pi$-cyclopentadienyldicarbonylisobutyryliron in place of $\pi$-cyclopentadienyldicarbonylacetyliron.

(($\pi$—C$_5$H$_5$) (OC)Fe[C(O)CH(CH$_3$)$_2$][C(O)CH$_3$])$_3$Al

Example 19

(Cis-diacetyltetracarbonylrhenate) hydrogen is prepared by mixing together 0.50 g (1.36 millimoles) of acetylpentacarbonylrhenium in 10 milliliters of diethyl ether at 0° C. with 1.36 millimoles of methyllithium solution in diethyl ether over a 10 minute period followed by stirring the reaction solution at 0° C. for an additional 45 minutes at which time the reaction solution is cooled to −78° C. and is treated with 1.36 millimoles of anhydrous hydrogen chloride in diethyl ether. After stirring the reaction solution at −78° C. for 10 minutes more, the stirring is continued at 0° C. for 1 hour. The solvent is removed at reduced pressure and the product is isolated by extraction into hexane solution followed by filtration and removal of the solvent from the filtrate. The product is air stable for at least 12 hours and melts when heated to 66° – 68° C. The product cis - $(OC)_4Re[C(CH_3)O \ldots H \ldots OC(CH_3)]$ or cis-$((OC)_4Re[C(O)CH_3][C(O)CH_3])H$ has the empirical formula $Re\ O_6\ C_8\ H_7$. The product is soluble in saturated hydrocarbons such as cyclohexane, hexane, pentane, octane, dodecane and unsaturated hydrocarbons such as benzene, toluene, xylene, mesitylene and chlorocarbon solvents such as methylene chloride, chloroform, carbon tetrachloride, and in methanol, acetone, diethyl ether, carbon disulfide, tetrahydrofuran, pyridine and ethyl acetate.

Figure 2:
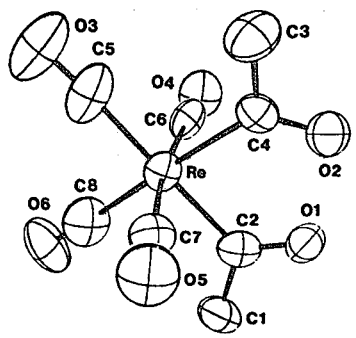
FIG. 2 is a perspective view of the molecular structure of one of the independent molecules of cis — $(OC)_4\ Re[C(CH_3)\ O\text{---}H\text{---}OC(CH_3)]$, showing the atomic numbering scheme, excluding the hydrogen atoms.

The three-dimensional molecular structure, excluding the hydrogen atoms, is shown in FIG. 2.

The structure of the product (cis-diacetyltetracarbonylrhenate) hydrogen is proven by the following:

(A) The proper elemental analysis;

(B) Nuclear magnetic resonance data. A single $H^1$—NMR peak at 7.22 $\tau$ and a single $H^1$—NMR peak at $-11.79$ $\tau$ in carbon disulfide solution in accordance with the two equivalent methyl groups and the enol proton, respectively;

(C) Infrared spectroscopic data. Four peaks due to the carbon monoxide ligands at 2095 cm$^{-1}$, 2005 cm$^{-1}$, 1990 cm$^{-1}$, 1965 cm$^{-1}$, in accordance with a cis-disubstituted octahedral complex containing four other carbon monoxide ligands, and a band at 1520 cm$^{-1}$ from the carbon — oxygen bond stretch of the coordinated acetyl groups all recorded in cyclohexane solution;

(D) The complete single-crystal X-ray structural determination of the crystal and the molecular structure. This evidence demonstrates the only slightly distorted octahedral local symmetry about the rhenium atom, the essentially planar and symmetrical nature of the ligand ring, the very short oxygen — oxygen "bite" distance, and the close contact of an oxygen atom of an adjacent molecule both supporting the presence of the hydrogen atom.

Example 20

This product is prepared by the procedure of EXAMPLE 19 using isobutyrylpentacarbonylrhenium in place of acetylpentacarbonylrhenium $((OC)_4Re[C(O)CH(CH_3)_2][C(O)CH_3])\ H$

Example 21

This product is prepared by the procedure of EXAMPLE 19 using $\pi$-cyclopentadienyldicarbonylacetyliron in place of acetylpentacarbonylrhenium and using a $-50°$ C. temperature in place of a 0° C. temperature.

$((\pi\text{-}C_5H_5)\ (OC)Fe[C(O)CH_3][C(O)CH_3])\ H$

Example 22

This product is prepared by the procedure of EXAMPLE 21 using $\pi$-cyclopentadienyldicarbonylisobutyryliron in place of $\pi$-cyclopentadienyl-dicarbonylacetyliron.

$((\pi\text{-}C_5H_5)\ (OC)Fe[C(O)CH(CH_3)_2][C(O)CH_3])\ H$

Example 23

This product may be prepared by a procedure which is analogous to that used for the preparation of acetylacetonate boron difluoride by adding a solution of 4 millimoles of boron trifluoride in 5 milliliters of diethyl ether to a solution of 4 millimoles of (cis-diacetyltetracarbonylrhenate) hydrogen in 5 milliliters of diethyl ether at $-78°$ C. and then stirring for 1 hour. The reaction solution is stirred at 0° C. for an additional hour. The solvent is removed at reduced pressure and the product is isolated by extraction into hexane solution followed by filtration and removal of the solvent from the filtrate.

$((OC)_4Re[C(O)CH_3][C(O)CH_3]BF_2$

Example 24

This product may be prepared by a procedure which is analogous to that used for the preparation of tris(acetylacetonate) silicon tetrafluoroborate; following the procedure of EXAMPLE 23 but using 1.33 millimoles of anhydrous silicon tetrachloride in place of the 4 millimoles of boron trifluoride and tetrahydrofuran as the solvent in place of diethyl ether and by isolating the product by extracting the reaction residue into 10 milliliters of tetrahydrofuran and then adding 1.33 millimoles of silver tetrafluoroborate in 5 milliliters of tetrahydrofuran at 0° C. followed by filtration and removal of the solvent of the filtrate at reduced pressure.

$((OC)_4Re[C(O)CH_3][C(O)CH_3]_3Si^+BF_4^-$

The metal compounds of the present invention have utility in a number of relationships, for example as catalysts, anti-knock agents, insecticides and as a source of finely divided metals. In catalysis the fact that these compounds are soluble in a variety of organic solvents such as hydrocarbons, e.g. heptane, ethers, such as diethyl ether and tetrahydrofuran, aromatic hydrocarbons, e.g. benzene, and chlorocarbon solvents, such as methylene chloride, permits the use of the catalyst in a homogeneous system. The neutral compounds, which are insoluble in aqueous solvent media, and the ionic compounds, which are insoluble in nonpolar organic solvents, permit the use of the catalyst in a heterogeneous system. The cobalt complex is an example of a compound which is useful in the carbonylation reaction of olefins having up to 14 carbon atoms to give aldehydes and alcohols which have one more carbon atom than the olefins. The aluminum complex is an example of a compound which is useful in the polymerization, isomerization and metathetical exchange reactions of various substrate feedstocks.

Other applications of the compounds of the present invention are the catalysis of the polymerization of ethylenic and acetylenic compounds to obtain polymers of higher molecular weight, and also as hydrogenation catalysts, such as for the saturation of olefinic or acetylenic compounds as well as the hydrogenation of CO bonds to obtain alcohols.

The metal containing compounds defined above also provide a convenient source for active forms of such metals in very finely divided form as the result of the thermal decomposition of the compounds.

What is claimed is:

1. A compound having the formula:

$$(L_aM[C(X)A][C(Y)B])_bM'$$

wherein
- M is a transition metal;
- M' is any metal, except lithium, magnesium or boron, or a proton;
- L is a coordinating ligand selected from the group consisting of at least one of CO, $PF_3$, $PCl_3$, $PR_3$, $P(OR)_3$, $AsR_3$, NCO, CN, $NR_3$, halogen, R, OR, CNR, NO, C(O)R, in unsaturated form, having from 1 to 20 carbon atoms;
- X and Y are each an atom or radical selected from the group consisting of at least one of O, S, NR, Se, PR;
- A and B are substituents each consisting of at least one of R, OR, $NR_2$, SR, SeR, $PR_2$, CN, $CF_3$;
- R is a saturated hydrocarbyl radical having from 1 to 20 carbon atoms or an unsaturated hydrocarbyl radical having from 2 to 20 carbon atoms;
- $a$ is an integer from 1 to 10, inclusive;
- $b$ is an integer from 1 to 6, inclusive.

2. The compound according to claim 1, wherein L is selected from the group consisting of CO, $RNC(OC)_3$ and $(\pi-C_5H_5)$ (OC).

3. The compound according to claim 2, wherein $L_a$ is $(OC)_4$.

4. The compound according to claim 1 wherein X is O.

5. The compound according to claim 1, wherein Y is O.

6. The compound according to claim 5, wherein X is O.

7. The compound according to claim 1, wherein A is a substituent selected from the group consisting of R and OR.

8. The compound according to claim 7, wherein A is R.

9. The compound according to claim 1, wherein B is a substituent selected from the group consisting of R and $NR_2$.

10. The compound according to claim 9, wherein B is R.

11. The compound according to claim 10, wherein A is R.

12. The compound according to claim 1, wherein A is a substituent selected from the group consisting of $CH_3$, $CH(CH_3)_2$, $CH_3CH_2$, $CH_2(C_6H_5)$ and $OC_2H_5$.

13. The compound according to claim 12, wherein A is $CH_3$.

14. The compound according to claim 1, wherein B is a substituent selected from the group consisting of $CH_3$, $CH_3(CH_2)_3$, and $N(CH_3)_2$.

15. The compound according to claim 14, wherein B is $CH_3$.

16. The compound according to claim 15, wherein A is $CH_3$.

17. The compound according to claim 1, wherein M is a transition metal selected from the group consisting of Mn, Fe and Re.

18. The compound according to claim 1, wherein M is Mn.

19. The compound according to claim 1, wherein M' is a metal selected from the group consisting of Al, Ga, Sc, Co, and Zn; and H.

20. The compound according to claim 19, wherein M' is Al.

21. The compound according to claim 19, where M' is H.

22. The compound according to claim 2, wherein X is O, Y is O, A is a substituent from the group consisting of R and OR, and B is a substituent from the group consisting of R and $NR_2$.

23. The compound according to claim 22, wherein A is a substituent from the group consisting of $CH_3$, $CH(CH_3)_2$, $CH_3CH_2$, $CH_2(C_6H_5)$, $OC_2H_5$; and B is a substituent from the group consisting of $CH_3$, $CH_3(CH_2)$ and $N(CH_3)_2$.

24. The compound according to claim 23, wherein M is a transition metal selected from the group consisting of Mn, Fe and Re.

25. The compound according to claim 24, wherein M' is a metal selected from the group consisting of Al, Ga, Sc, Co, and Zn; and H.

26. The compound according to claim 25 wherein M is Mn.

27. The compound according to claim 25, wherein M' is Al.

28. The compound according to claim 25 wherein M' is H.

29. The compound according to claim 25, wherein A is $CH_3$.

30. The compound according to claim 25, wherein B is $CH_3$.

31. The compound according to claim 25, wherein M is Mn and M' is Al.

32. The compound according to claim 25, wherein M is Mn and $L_a$ is selected from the group consisting of $(OC)_4$ and $RNC(OC)_3$.

33. The compound according to claim 25, wherein M is Fe and $L_a$ is $(\pi-C_5H_5)$ (OC).

34. A process for the production of $$(L_aM[C(X)A][C(Y)B])_bM'$$

wherein
- M is a transistion metal;
- M' is any metal, except lithium or magnesium, or a proton;
- L is a coordinating ligand selected from the group consisting of at least one of CO, $PF_3$, $PCl_3$, $PR_3$, $P(OR)_3$, $AsR_3$, NCO, CN, $NR_3$, halogen, R, OR, CNR, NO, C(O)R, in unsaturated form, having from 1 to 20 carbon atoms;
- X and Y are each an atom or radical selected from the group consisting of at least one of O, S, NR, Se, PR; A and B are substituents each consisting of at least one of R, OR, $NR_2$, SR, SeR, $PR_2$, CN;
- R is a saturated or unsaturated hydrocarbyl radical having from 1 to 20 carbon atoms;
- $a$ is an integer from 1 to 10, inclusive;
- $b$ is an integer from 1 to 6, inclusive; which comprises the steps of admixing in an inert atmosphere the approximately stoichiometric proportions of a metal complex $L_aM[C(X)A][CY]$ with a source of B anion, adding to the mixture a complex of M', maintaining the temperature in the range of $-78°$ C. to $0°$ C., then quenching the reaction by removal of the solvent, and extracting the product.

35. The compound according to claim 31, wherein $L_a$ is $(OC)_4$, A is $CH_3$, B is $CH_3$, and $b=3$, and in which the acetyl groups are cis.

36. The compound according to claim 25, wherein M is Re, M' is H, $L_a$ is $(OC)_4$, A is $CH_3$, B is $CH_3$, and $b=1$, and in which the acetyl groups are cis.

37. A compound having the formula $((OC)_4Re[C(O)CH_3][C(O)CH_3]) BF_2$

38. A compound having the formula $((OC)_4Re[C(O)CH_3][C(O)CH_3])_3Si^+BF_4^-$

* * * * *